US008234077B2

(12) United States Patent
Anastassiou et al.

(10) Patent No.: US 8,234,077 B2
(45) Date of Patent: Jul. 31, 2012

(54) METHOD OF SELECTING GENES FROM GENE EXPRESSION DATA BASED ON SYNERGISTIC INTERACTIONS AMONG THE GENES

(75) Inventors: Dimitris Anastassiou, Tenafly, NJ (US); Vinay Varadan, Hastings-on-Hudson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 508 days.

(21) Appl. No.: 12/307,694

(22) PCT Filed: May 10, 2007

(86) PCT No.: PCT/US2007/068666
§ 371 (c)(1),
(2), (4) Date: May 4, 2009

(87) PCT Pub. No.: WO2007/134167
PCT Pub. Date: Nov. 22, 2007

(65) Prior Publication Data
US 2009/0299643 A1    Dec. 3, 2009

Related U.S. Application Data

(60) Provisional application No. 60/799,271, filed on May 10, 2006, provisional application No. 60/885,349, filed on Jan. 17, 2007.

(51) Int. Cl.
*G01N 33/48* (2006.01)
*C12Q 1/68* (2006.01)
*G06F 7/60* (2006.01)
*G06G 7/58* (2006.01)

(52) U.S. Cl. ............... 702/19; 435/6; 702/20; 703/2; 703/11

(58) Field of Classification Search ............ None
See application file for complete search history.

(56) References Cited

U.S. PATENT DOCUMENTS

| | | | |
|---|---|---|---|
| 3,286,177 | A | 11/1966 | Boer et al. |
| 3,354,297 | A | 11/1967 | Anderson et al. |
| 3,449,553 | A | 6/1969 | Swan |
| 3,535,084 | A | 10/1970 | Keisuke et al. |
| 5,597,719 | A | 1/1997 | Freed et al. |
| 5,715,821 | A | 2/1998 | Faupel |
| 6,110,109 | A | 8/2000 | Hu et al. |
| 6,996,476 | B2 | 2/2006 | Najarian |
| 2003/0104463 | A1 | 6/2003 | Schuermann et al. |
| 2003/0215866 | A1 | 11/2003 | Liebovitch et al. |
| 2004/0241730 | A1 | 12/2004 | Yakhini et al. |
| 2004/0253637 | A1 | 12/2004 | Buechler et al. |
| 2007/0178526 | A1 | 8/2007 | Kountakis et al. |
| 2007/0299645 | A1 | 12/2007 | Shapiro et al. |
| 2009/0012719 | A1 | 1/2009 | Anastassiou et al. |
| 2009/0299643 | A1 | 12/2009 | Anastassiou et al. |

FOREIGN PATENT DOCUMENTS

| | | |
|---|---|---|
| WO | WO 2004/019264 | 3/2004 |
| WO | WO 2007/067956 | 6/2007 |
| WO | WO 2007/134167 | 11/2007 |

OTHER PUBLICATIONS

U.S. Appl. No. 12/022,862, filed Jan. 30, 2008.
U.S. Appl. No. 12/133,045, filed Jun. 4, 2008.
U.S. Appl. No. 13/013,321, filed Jan. 25, 2011.
U.S. Appl. No. 12/022,862, Feb. 20, 2008 Missing Parts.
U.S. Appl. No. 12/022,862, Sep. 22, 2008 Response to Missing Parts.
U.S. Appl. No. 12/022,862, Sep. 17, 2010 Restriction Requirement.
U.S. Appl. No. 12/022,862, Dec. 14, 2010 Response to Restriction Requirement.
U.S. Appl. No. 12/022,862, Feb. 18, 2011 Non-Final Office Action.
U.S. Appl. No. 12/133,045, Jun. 19, 2008 Missing Parts.
U.S. Appl. No. 12/133,045, Aug. 19, 2008 Response to Missing Parts.
U.S. Appl. No. 12/133,045, Nov. 15, 2010 Non-Final Office Action.
U.S. Appl. No. 12/133,045, Feb. 15, 2011 Response to Non-Final Office Action.
U.S. Appl. No. 13/013,321, Feb. 10, 2011 Notice to File Corrected Application Papers.
U.S. Appl. No. 13/013,321, Mar. 1, 2011 Response to Notice to File Corrected Application Papers.
Bassett et al., 1999, "Gene Expression Informatics—It's All in Your Mine", *Nature Genetics Supplement*, vol. 21, pp. 51-55.
Bi et al., 2004, "Bipartite pattern discovery by entropy minimization-based multiple local alignment," *Nucleic Acids Research*, vol. 32, No. 17: pp. 4979-4991.
Boser, B.E., Guyon, I.M. & Vapnik, V.N.; A training algorithm for optimal margin classifiers, in $5^{th}$ Annual Workshop con COLT, (ed. Haussler, D.) pp. 144-152, ACM Press 1992.
Brazma et al., 2000, "Gene Expression Data Analysis", *FEBS Lett.*, vol. 480, pp. 17-24.
Eisen, M.B., Spellman, P.T., Brown, P.O. & Botstein, D.; Cluster analysis and display of genome-wide expression patterns; *Proc Natl Acad WSci USA* 95, pp. 14863-14868; 1998.
U.S. Appl. No. 12/133,045, Apr. 13, 2011 Final Office Action.
Irizarry, R.A. et all; Exploration, normalization, and summaries of high density oligonucleotide array probe level data; *Biostatistics* 4, pp. 249-264; 2003.
International Search Report—Application No. PCT/US2006/061749 (Feb. 5, 2008).

(Continued)

*Primary Examiner* — Shubo Zhou
(74) *Attorney, Agent, or Firm* — Baker Botts L.L.P.

(57) ABSTRACT

A method is provided for selecting two or more genes from gene expression data. In the method, gene expression data for a plurality of genes is provided, where the gene expression data include expression levels for each of the plurality of genes. The gene expression data is discretized. Based on the discretized gene expression data, the synergy among the plurality of genes with respect to a phenotype, for example, presence or absence of a disease in a tissue, is evaluated. Two or more genes whose synergy exceeds a predetermined threshold are selected. A system implementing the method is also provided.

13 Claims, 4 Drawing Sheets

OTHER PUBLICATIONS

International Search Report—Application No. PCT/US2007/06866 (Aug. 5, 2008).

U.S. Appl. No. 12/133,045, Feb. 23, 2012 Response to Final Office Action and Terminal Disclaimer.

U.S. Appl. No. 12/133,045, Aug. 30, 2011 Non-Final Office Action.

U.S. Appl. No. 12/133,045, Jul. 13, 2011 Amendment and Request for Continued Examination (RCE).

U.S. Appl. No. 12/022,862, Sep. 6, 2011 Notice of Allowance.

U.S. Appl. No. 12/022,862, Jun. 9, 2011 Response to Non-Final Office Action.

U.S. Appl. No. 12/133,045, Dec. 15, 2011 Final Office Action.

U.S. Appl. No. 12/133,045, Nov. 30, 2011 Response to Non-Final Office Action.

U.S. Appl. No. 12/022,862, Nov. 23, 2011 Issue Fee payment.

Furlanello et al., 2003, "Entropy-based gene ranking without selection bias for the predictive classification of microarray data," *BMC Bioinformatics*, 4:54.

Hamer et al., 2003 "Rational Design of Drugs That Induce Human Immunodeficiency Virus Replication," *Journal of Virology*, vol. 77, No. 19: p. 10227-10236.

Liu et al., 2005, "An Entropy-based gene selection method for cancer classification using microarray data," *BMC Bioinformatics*, 6:76.

Mootha, V.K. et al.; PGC-1alpha-responsive genes involved in oxidative phosphorylation are coordinately downregulated in human diabetes; *Nat Genet* 34; pp. 267-273; 2003.

Rhodes, D.R. & Chinnaiyan, A.M.; Integrative analysis of the cancer transcriptome; *Nat GenetI; 37 Suppl*, pp. S31-S37; 2005.

Rhodes, D.R. et al.; Mining for regulatory programs in the cancer transcriptome; *Nat Genet* 37; pp. 579-583; 2005.

Segal, E., Friedman, N., Koller, D. & Regev A.; A module map showing conditional activity of expression modules in cancer; *Nat Genet* 36; pp. 1090-1098; 2004.

Subramanian, A. et al.; Gene set enrichment analysis: a knowledge-based approach for interpreting genome-wide expression profiles; *Proc Natl Acad Sci U S.A.*; 103; pp. 15545-15550; 2005.

Tomlins, S.A. et al.; Integrative molecular concept modeling of prostate cancer progression; *Nat Genet* 39,pp. 41-51; 2007.

Cover, T.M. & Thomas, J.A.; *Elements of information theory*; xxiii, p. 748 (Wiley-Interscience; Hoboken, NJ); 2006.

Varadan, V. & Anastassiou, D.; Inference of disease-related molelcular logic from systems-based microarray analysis; *PLoS comput Biol* 2; pp. e681 2006.

Varadan, V., Miller, D.M., $3^{rd}$ & Anastassiou, D.; Computational inference of the molecular logic for synaptic connectivity in C. elegans 22; pp. e497-e506; 2006.

Singh, D. et al.; Gene expression correlates of clinical prostate cancer behavior; *Cancer Cel 1*, pp. 203-209; 2002.

Farias, E.F., Marzan, C. & Mira-y-Lopez, R.; Cellular retinol-binding protein-I inhibits PI3K/Akt signaling through a retinoic acid receptor-dependent mechanism that regulates p. 85-p. 110 heterodimerization; *Oncogene* 24; pp. 1598-1606; 2005.

U.S. Appl. No. 13/489,334, filed Jun. 5, 2012.

U.S. Appl. No. 12/133,045, filed Jun. 5, 2012 Issue Fee payment.

METHOD OF SELECTING GENES FROM GENE EXPRESSION DATA BASED ON SYNERGISTIC INTERACTIONS AMONG THE GENES

CROSS-REFERENCE TO RELATED APPLICATIONS

The present application is a national phase of International Application PCT/US07/68666, filed May 10, 2007, which claims priority to U.S. Provisional Application Ser. No. 60/799,271 filed May 10, 2006 and U.S. Provisional Application Ser. No. 60/885,349 filed Jan. 17, 2007, the entire contents of which are incorporated by reference herein.

BACKGROUND

The disclosed subject matter relates generally to systems and methods for factor selection, including factors useful in gene expression analysis.

The expression levels of thousands of genes, measured simultaneously using DNA microarrays, can provide information useful for medical diagnosis and prognosis. However, gene expression measurements have not provided significant insight into the development of therapeutic approaches. This can be partly attributed to the fact that while traditional gene selection techniques typically produce a "list of genes" that are correlated with disease, they do not reflect interrelationships.

Gene selection techniques based on microarray analysis often involve individual gene ranking depending on a numerical score measuring the correlation of each gene with particular disease types. The expression levels of the highest-ranked genes tend to be either consistently higher in the presence of disease and lower in the absence of disease, or vice versa. Such genes usually have the property that their joint expression levels corresponding to diseased tissues and the joint expression levels corresponding to healthy tissues can be cleanly separated into two distinct clusters. These techniques are therefore convenient for classification purposes between disease and health, or between different disease types. However, they do not identify cooperative relationships or the synergy among multiple interacting genes.

There is therefore a need for the ability to analyze genes in terms of the cooperative, as opposed to independent, nature of their contributions towards a phenotype.

SUMMARY

The disclosed subject matter provides techniques for the analysis of the cooperative interactions or synergy among multiple interacting factors. The factors can be features, elements or outcomes that are cooperatively associated with one or more factors or outcomes by their joint presence or absence.

In some embodiments of the disclosed subject matter, methods for selecting factors from a data set of measurements are provided. The measurements can include values of factors and/or outcomes. Two or more factors that are jointly associated with one or more outcomes from the data set are identified. Each of the two or more factors are analyzed to determine at least one cooperative interaction among the factors with respect to an outcome or factor. The factors can be a module of factors or a sub-module of factors. The interaction can be a structure of interactions.

The factors can include two or more genes. The data set can include gene expression data including expression levels for each of the genes. The outcomes includes presence or absence of a disease, and the genes can be a module of genes, preferably a smallest cooperative module of genes with joint expression levels that can be used for a prediction of the presence of a disease with high accuracy.

In other embodiments of the disclosed subject matter, methods for selecting two or more genes from gene expression data are provided. The gene expression data can include expression levels for each of the two or more genes. The method includes providing gene expression data for two or more genes, discretizing the gene expression data, identifying the two or more genes with a high synergy, and identifying a cooperative interaction that connects the expression levels in the two or more genes with presence or absence of a disease. The gene expression data can be derived from at least one microarray of gene expression data. The genes can be a module of genes. The cooperative interaction can be modeled using a Boolean function, a parsimonious Boolean function, or the most parsimonious Boolean function. The high synergy can be a maximum synergy.

In other embodiments of the disclosed subject matter, systems for selecting two or more genes from gene expression data are provided. The gene expression data includes expression levels for each of the two or more genes. The system includes at least one processor, a computer readable medium coupled to the processor including instructions which when executed cause the processor to provide gene expression data for the genes. The instructions also cause the processor to discretize the gene expression data, choose a single threshold for each of the two or more genes, identify the two or more genes with a high synergy, and identify a cooperative interaction that connects the expression levels in the two or more genes with presence of a disease. The gene expression data can be derived from a microarray of gene expression data. The two or more genes can be a module of genes. The high synergy can be a maximum synergy.

In other embodiments of the disclosed subject matter, systems for selecting factors from a data set of measurements are provided. Each measurement can include values of the factors and outcomes. The system includes at least one processor and a computer readable medium coupled to the at least one processor. The computer readable medium includes instructions which when executed cause the processor to identify two or more factors that are jointly associated with one or more outcomes or factors from the data, and, analyze each of the two or more factors to determine at least one cooperative interaction among the factors with respect to an outcome or factor. The factors can be a module of factors. The module of factors can include at least one sub-module of factors. The cooperative interaction can include a structure of interactions, such as a logic function.

The two or more factors can be two or more genes, the data can include gene expression data including expression levels, and the outcomes can be the presence or absence of a disease. The genes can be a module of genes. The module of genes can include at least one sub-module of genes. The module of genes can be a smallest module of genes with joint expression levels that can be used for a prediction of the presence of disease.

DETAILED DESCRIPTION

According to some aspects of the disclosed subject matter, a method for selecting factors from a data set of measurements is provided. The method includes identifying factors cooperatively associated with an outcome from a data set for two or more factors, and analyzing each of the factors or modules of factors to determine cooperative or synergistic interactions among the factors or outcomes with respect to the outcome. The data set can be a set of measurements that includes values of the factors and the outcomes.

One application of the disclosed subject matter is where the factors are genes and the inference of the cooperative relationship or synergy among multiple interacting genes is desired. Although the following will describe disease data it can be more generally applicable to other data sets.

Other applicable data sets include other biological data such as how cells are influenced by stimuli jointly, financial data, internet traffic data, scheduling data for industries, marketing data, and manufacturing data, for example. Table 1, below, specifies other data sets relevant to various objectives, including factors and outcomes, to which the disclosed subject matter can also be applied:

TABLE 1

| Objective | Factors | Outcomes |
| --- | --- | --- |
| Disease pathway identification | Gene expression | Disease |
| Synaptic specificity factors | Gene expression | Neural synapses |
| Disease susceptibility of specific genotypes | Single Nucleotide Polymorphisms (SNPs) | Disease |
| Genotypic basis for gene expression profiles | SNPs | Gene expression |
| Gene regulation factors | Gene expression | Gene expression |
| Gene expression association with individual SNPs | Gene expression | SNP |
| Pharmacogenomics | SNPs | Drug resistance |
| Drug side-effect modeling | SNPs | Side effect of drug |
| Stocks/bonds/currency selling/buying price identification | Stocks/bonds/currency price time series data | Sell/Buy at given price |
| Macroeconomic models | Macroeconomic time series such as consumer index, housing market index, trade balance, etc | Federal interest rate increase/decrease |

Figure 1:
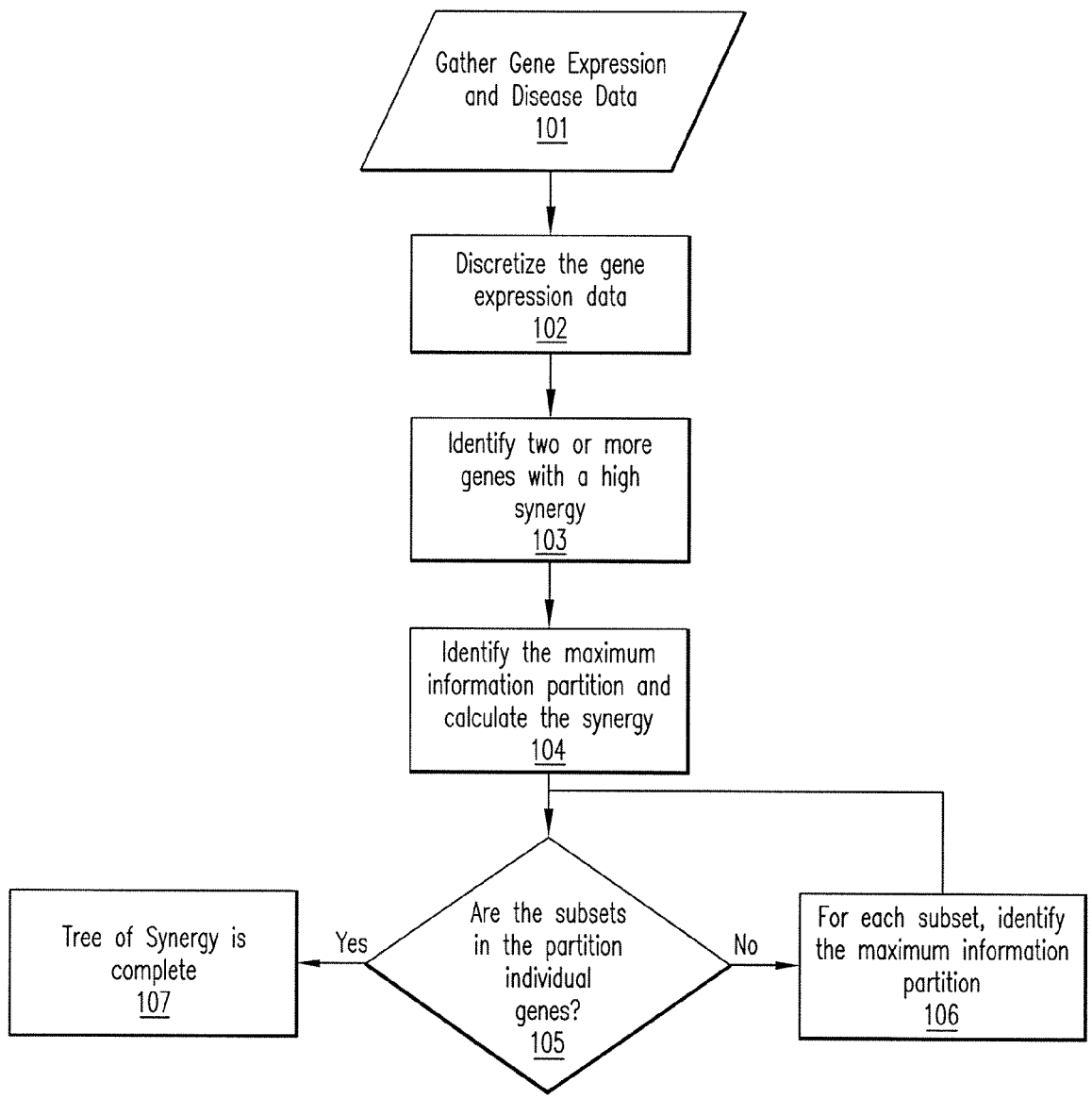
FIG. 1 is a diagram according to some embodiments of the disclosed subject matter.

Referring to FIG. 1, gene expression data for two or more genes is provided 101 in the form of, for example, a microarray of expression data. The gene expression data is then discretized 102. For example, the data can be binarized into two levels. Other levels of discretization, such as trinarization, can also be used.

Rather than independently binarizing each gene's expression level, which can be more appropriate for an individual gene ranking approach, single thresholds are used for the genes. This approach is consistent with the fact that finding global interrelationships among genes is desirable and that the microarray data have already been normalized across the tissues and genes. Therefore, a choice of high threshold will identify the genes that are "strongly" expressed, while a choice of a low threshold will identify the genes that are expressed even "weakly." Entropy Minimization and Boolean Parsimony ("EMBP") analyses can be performed across several thresholds and to determine the threshold levels that provide optimized performance, as disclosed in International Application No. PCT/US06/61749, the disclosure of which is incorporated herein by reference.

Following binarization, each gene can be assumed to be either expressed or not expressed in a particular tissue. It can also be assumed that there are two types of tissues, either healthy ones or tissues suffering from a particular disease. For example, Table 2, below shows results from hypothetical microarray measurements of three genes, $G_1$, $G_2$, and $G_3$ in both the presence and absence of a particular cancer C. $N_0$ and $N_1$ represent the presence and absence of cancer, respectively.

TABLE 2

| $G_1$ | $G_2$ | $G_3$ | $N_0$ | $N_1$ |
| --- | --- | --- | --- | --- |
| 0 | 0 | 0 | 2 | 6 |
| 0 | 0 | 1 | 0 | 24 |
| 0 | 1 | 0 | 2 | 7 |
| 0 | 1 | 1 | 0 | 26 |
| 1 | 0 | 0 | 1 | 7 |
| 1 | 0 | 1 | 0 | 25 |
| 1 | 1 | 0 | 76 | 1 |
| 1 | 1 | 1 | 19 | 4 |

The latter assumption can also be generalized to include more than two types of tissues, or modified to be used for classification among several types of cancer. According to one aspect of the disclosed subject matter, two or more genes with a high synergy are identified 103, as detailed below.

Cooperative or synergistic interactions between multiple genes can then be determined 104, as shown in FIG. 1. Because systems biology is based on a holistic view of biological systems, synergy is important.

A gene set of n genes can have expression levels $G_1$, $G_2$, ..., $G_n$ and a particular outcome C can be any phenotype, such as the presence of a particular disease or the differentiation of stem cells into a particular cell type when analyzing expression data of human tissues. The synergy $Syn(G_1, G_2, ..., G_n; C)$ of the gene set with respect to the phenotype C is defined by equation (1):

$$I(G_1, G_2, ..., G_n; C) = \max_{\substack{\text{all partitions} \\ \{S_i\} \text{ such that} \\ \cup_i S_i = \{G_1, ..., G_n\} \\ \text{and } \cap_i S_i = \emptyset}} \sum_i I(S_i; C) \quad (1)$$

The partition of the gene set that is chosen in equation (1) above is the one that maximizes the sum of the amounts of mutual information connecting the subsets of that partition with the phenotype 104 as shown in FIG. 1, and it is referred to as the "synergistic partition" of the gene set $\{G_1, G_2, \ldots, G_n\}$ with respect to the phenotype C. The definition is consistent with the intuitive concept that synergy is the additional amount of contribution for a particular task provided by an integrated "whole" compared with what can best be achieved, after breaking the whole into "parts," by the sum of the contributions of these parts. The above quantity can be divided by the entropy H(C) from EMBP analysis, in which case the maximum possible thus normalized synergy will be +1.

For the special case of n=2, the synergy is defined as shown in equation (2):

$$Syn(G_1, G_2; C) = I(G_1, G_2; C) - [I(G_1, C) + I(G_2, C)]. \quad (2)$$

Equation (2) is symmetric with respect to the three random variables and equal to the opposite of the mutual information $I(G_1; G_2; C)$ common to the three variables $G_1$, $G_2$, C. Contrary to the mutual information common to two variables, the mutual information common to three variables is not necessarily a nonnegative quantity. This allows for a strictly positive synergy.

In one example, it can be assumed that each of the genes $G_1$ and $G_2$ is equally (50% of the time) expressed when C=1 and C=0. In that case, it would appear that the two genes are uncorrelated with the phenotype C, because $I(G_1; C) = I(G_2; C) = 0$, and the genes would not be found high up in any typical "gene ranking" computational method. However, C can to be determined with absolute certainty from the joint state of the two genes, for example when C=1 if $G_1 = G_2$, and C=0 if $G_1 \neq G_2$, in which case $I(G_1, G_2; C) = 1$, and the synergy is positive and equal to +1. On the other hand, if $G_1 = G_2 = C$ then the synergy is negative and equal to -1. More generally, if $G_1 = G_2 = \ldots = G_n = C$ (ultimate redundancy) then the multivariate synergy can become even more negative and equal to -(n-1).

Since $H(C|G_1, G_2, \ldots, G_n) = H(C) - I(G_1, G_2, \ldots, G_n; C)$, EMBP analysis naturally tends to find high-synergy results, although not necessarily the most synergistic ones.

In another example, as shown in Table 2, equation (3) can be used for n=3 and is simplified by omitting the phenotypes.

$$Syn_{123} = I_{123} - \max(I_1 + I_{23}, I_2 + I_{13}, I_3 + I_{12}, I_1 + I_2 + I_3) \quad (3)$$

The values for mutual information between gene subsets and the phenotype can then be found in this example as follows: $I_{123} = 0.7963$; $I_{12} = 0.7152$; $I_{13} = 0.5094$; $I_{23} = 0.5163$; $I_1 = 0.3235$; $I_2 = 0.3335$; and $I_3 = 0.2782$.

Positive synergy implies some form of direct or indirect interaction of the genes, as a system. This definition of synergy also allows for insight into the structure of potential pathways by making iterative use of the "synergistic partition," defined earlier, to generate a hierarchical decomposition of the gene set into smaller modules. In particular, consider a rooted and not necessarily binary tree with n leaves, each of which represents one of the genes. Each node of the tree represents a subset or sub-module of genes, which contains the genes represented by the leaves of the clade formed by the node. Therefore the root represents the whole gene set. The synergistic partition of the whole gene set, as defined above, can then be represented by the branching of the root, so that the nodes that are neighboring to the root represent the gene subsets or sub-modules defined by the synergistic partition 105, 106 as shown in FIG. 1. Some of these nodes can be leaves, representing a single gene. If they are not leaves, then they represent a subset of genes, which has its own synergistic partition, defined and evaluated as above, with respect to the phenotype. This methodology can be repeated for all gene subsets, until the full tree is formed 107 as outlined in FIG. 1. This is referred to as the tree of synergy of the gene set $\{G_1, G_2, \ldots, G_n\}$ with respect to the phenotype C. Each intermediate node of the tree of synergy identifies a gene subset or sub-module with nonnegative synergy.

Figure 2:
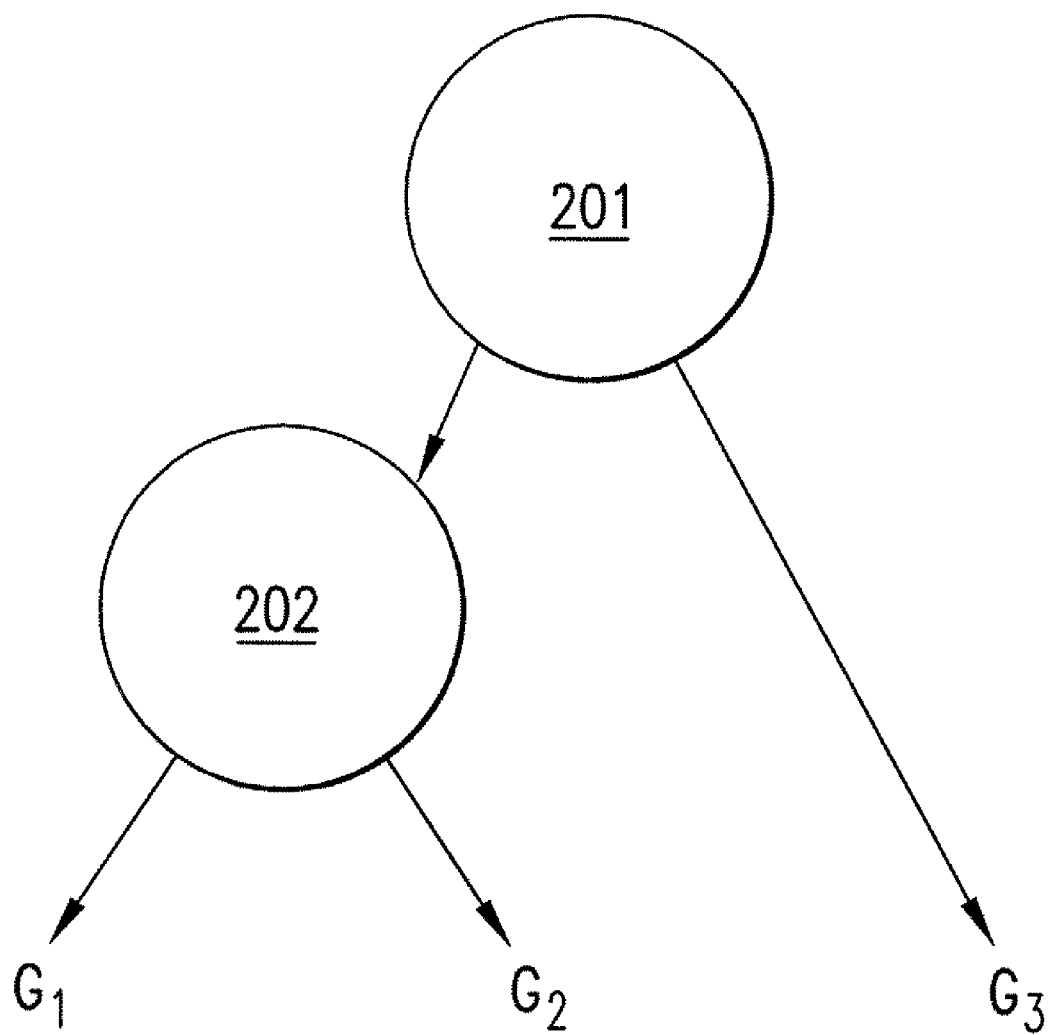
FIG. 2 is a diagram according to some embodiments of the disclosed subject matter.

As shown in FIG. 2, $G_1$ and $G_2$ can be a subset of genes or a module or sub-module of genes that together have a nonnegative synergy 202 and a third independent gene $G_3$ with a negative synergy 201 between itself and the subset of $G_1$ and $G_2$. In the example of Table 2, the synergy between $G_1$ and $G_2$ is +0.0582 and the synergy between the subset of $G_1$ and $G_2$ and $G_3$ is -0.1971.

The synergy, as defined above, refers to the combined cooperative participation of all n genes. If, for example, the expression of one of these genes is independent of all the other genes including the phenotype, then the synergy of the n-gene set will be zero, even if the set contains synergistic subsets or sub-modules. Therefore, for a thorough synergistic analysis of a gene set, it can be desirable to also identify the most synergistic subsets of size n-1, n-2, ..., 2, which may not necessarily appear in the tree of synergy. For n=3, however, it can be proved that the most synergistic subset of size 2, if it has positive synergy, is defined by an existing clade of the full tree of synergy. In this way, the disclosed subject matter identifies a cooperative or synergistic interaction that connects the expression levels in two or more genes with the presence or absence of disease. The interaction can be modeled using, for example, using a most parsimonious Boolean function as disclosed in International Application No. PCT/US06/61749.

Figure 3:
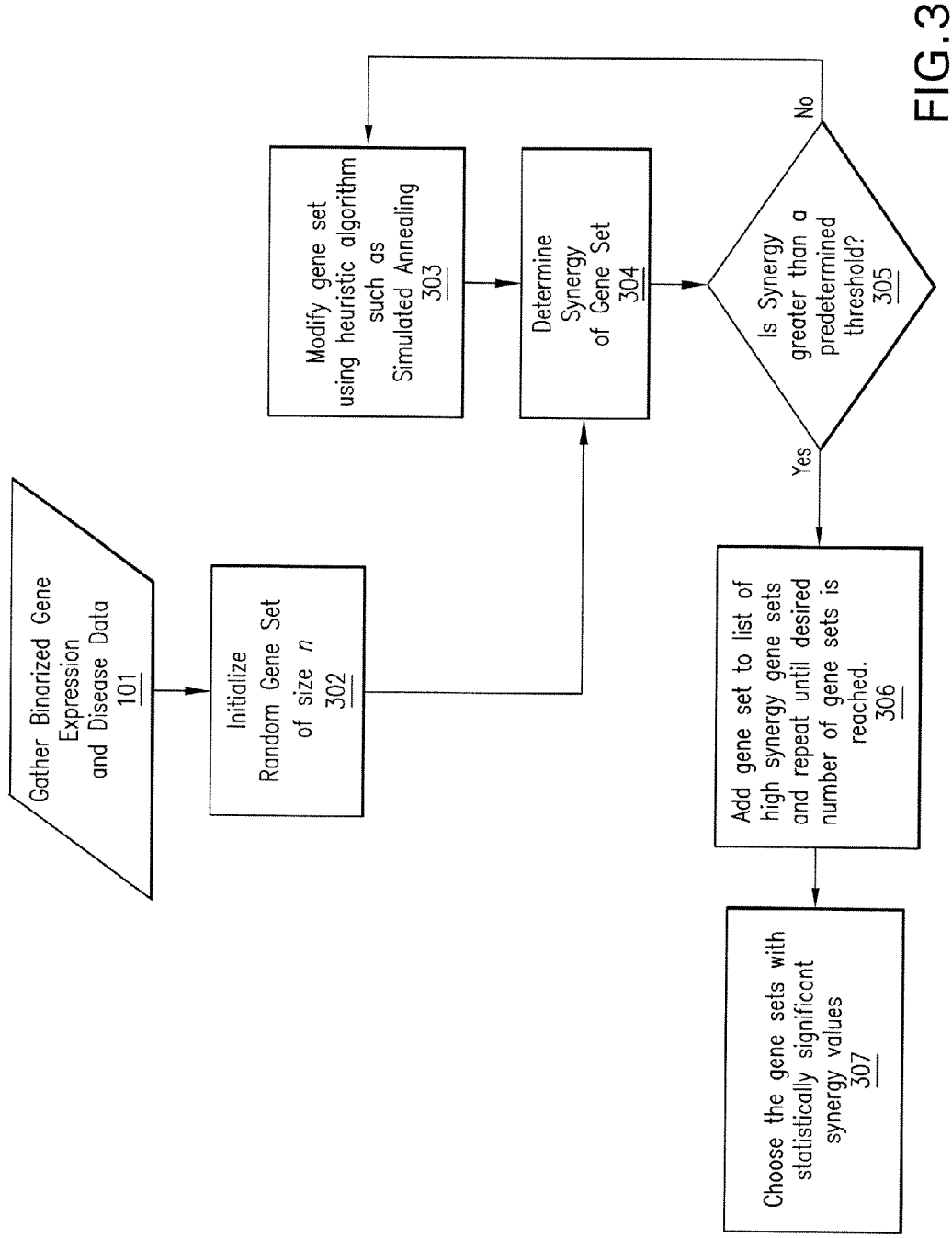
FIG. 3 is a diagram according to some embodiments of the disclosed subject matter.

For small gene set sizes n, such as 3 or 2, it is possible to identify all the synergistic sets of genes by doing a search of possible gene sets of size n. However, as the size increases, searches of all gene sets become computationally expensive and therefore heuristic methods can be employed to find a collection of gene sets with positive synergy, as shown in FIG. 3. Starting with the binarized gene expression data 301 an initial random gene set is first chosen 302 and the synergy of the gene set is calculated 304. If the synergy is greater than a predetermined threshold 305 the gene set is added to the list of gene sets with synergy. The predetermined threshold could be zero, for example. The gene set is then modified using a heuristic algorithm such as simulated annealing 303 to identify a new gene set whose synergy is evaluated 303. If the synergy of the new gene set is positive, it is added to the list of existing gene sets 306. This process is repeated until the desired number of gene sets is reached. The gene sets are then selected based on the statistical significance of their synergy values 307.

For small sizes of gene sets, synergistic analysis can be done with algorithms that list all the partitions of a particular set of genes. The total number of partitions of a set with n elements is given by the "Bell number." As the values of n increase, however, the increased computational complexity makes the problems more complex and heuristic solutions can be used to do the analysis.

The techniques of the disclosed subject matter can be implemented by way of off-the-shelf software such as MATLAB, JAVA, C++, or other software. Machine language or other low level languages can also be utilized. Multiple processors working in parallel can also be utilized.

Figure 4:
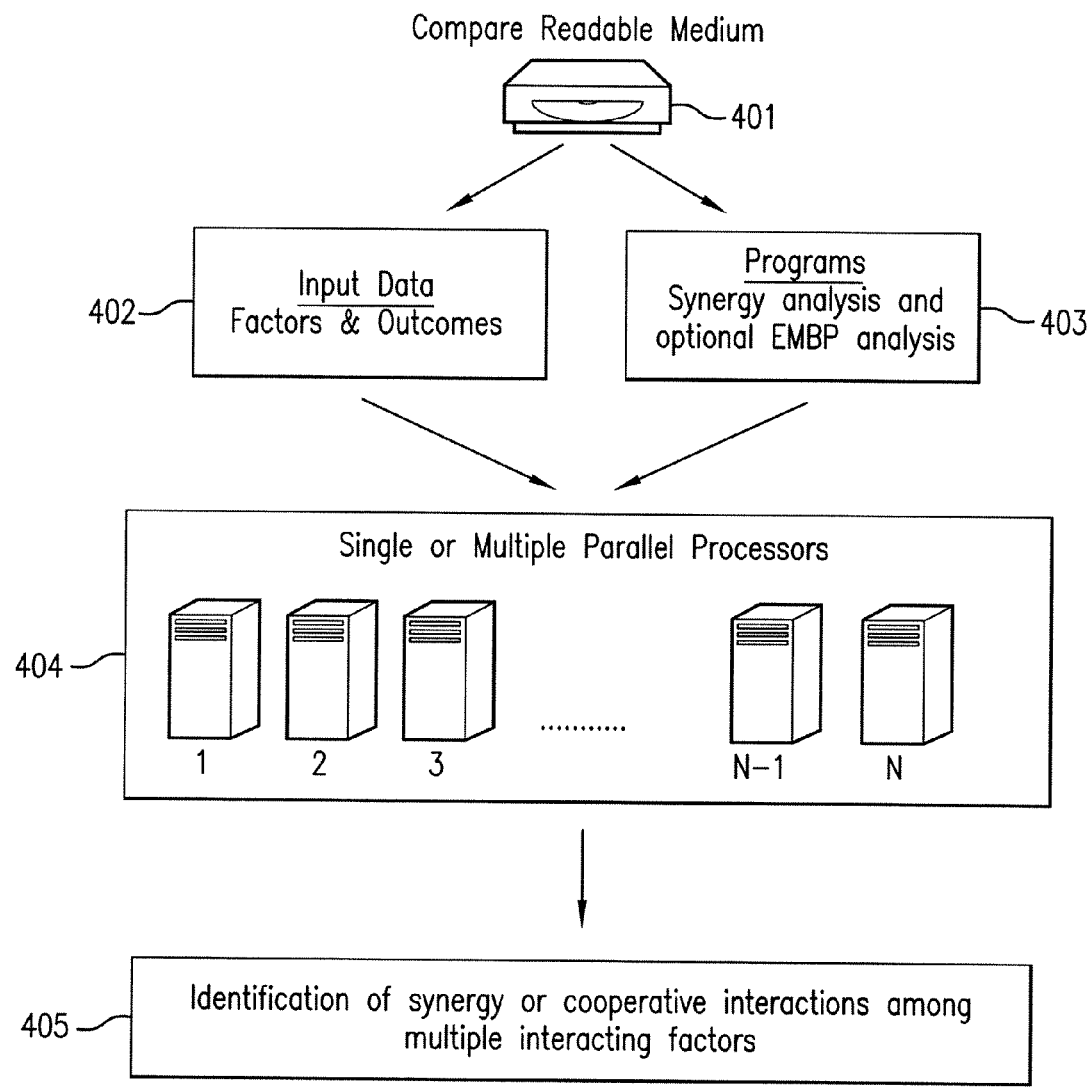
FIG. 4 is a schematic diagram according to some embodiments of the disclosed subject matter.

As illustrated in the embodiment depicted in FIG. 4, a system in accordance with the disclosed subject matter can include a processor or multiple processors 404 and a computer readable medium 401 coupled to the processor or processors 404. The computer readable medium includes data such as factors and outcomes 402 and can also include programs for synergy analysis and/or EMBP analysis 403. The system leads to the identification of the synergy, synergies or cooperative interaction(s) among multiple interacting factors 405. Multiple processors 404 working in parallel can also be utilized.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope of the disclosed subject matter.

What is claimed is:

1. A method for selecting two or more genes from gene expression data, comprising:
   providing gene expression data for a plurality of genes, the gene expression data comprising expression levels for each of the plurality of genes;
   discretizing the gene expression data;
   based on the discretized gene expression data, evaluating, using a computer processor, a synergy among the plurality of genes with respect to a phenotype; and
   selecting, from the plurality of genes, two or more genes whose synergy exceeds a predetermined threshold.

2. The method of claim 1, wherein the gene expression data is obtained from at least one microarray of gene expression analysis.

3. The method of claim 1 wherein the two or more genes comprise a module of genes.

4. The method of claim 1, wherein evaluating the synergy comprises using a most parsimonious Boolean function.

5. The method of claim 1, wherein selecting the two or more genes comprises selecting the two or more genes having a maximum synergy.

6. The method of claim 1, wherein the phenotype is presence or absence of a disease in a tissue.

7. The method of claim 1, wherein discretizing the gene expression data comprises binarizing the gene expression level for each of the plurality of genes.

8. The method of claim 7, wherein binarizing the gene expression level for each of the plurality of genes comprises selecting a single threshold gene expression level for all of the plurality of genes.

9. The method of claim 1, wherein evaluating the synergy of any subset of genes among the plurality of genes comprises evaluating mutual information connecting the subset of genes with the phenotype.

10. A system for selecting two or more genes from gene expression data, comprising:
    at least one processor, and a computer readable medium, coupled to the at least one processor, having stored thereon instructions which when executed cause the processor to:
    provide gene expression data for a plurality of genes, the gene expression data comprising expression levels for each of the plurality of genes;
    discretize the gene expression data;
    based on the discretized gene expression data, evaluate, using a computer processor, a synergy among the plurality of genes with respect to a phenotype in a tissue; and
    select, from the plurality of genes, two or more genes whose synergy exceeds a predetermined threshold.

11. The system of claim 10, wherein the gene expression data is obtained from at least one microarray of gene expression analysis.

12. The system of claim 10 wherein the two or more genes comprise a module of genes.

13. The system of claim 10, wherein selecting the two or more genes comprises selecting the two or more genes having a maximum synergy.

* * * * *